United States Patent
Chen et al.

(10) Patent No.: US 11,085,988 B2
(45) Date of Patent: Aug. 10, 2021

(54) METHOD FOR ESTIMATING SYSTEMATIC IMPERFECTIONS IN MEDICAL IMAGING SYSTEMS WITH DEEP LEARNING

(71) Applicant: The Board of Trustees of the Leland Stanford Junior University, Stanford, CA (US)

(72) Inventors: Feiyu Chen, Mountain View, CA (US); Christopher Michael Sandino, Menlo Park, CA (US); Joseph Yitan Cheng, Santa Clara, CA (US); John M. Pauly, Stanford, CA (US); Shreyas S. Vasanawala, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 16/824,565

(22) Filed: Mar. 19, 2020

(65) Prior Publication Data
US 2020/0300957 A1 Sep. 24, 2020

Related U.S. Application Data

(60) Provisional application No. 62/820,941, filed on Mar. 20, 2019.

(51) Int. Cl.
| | |
|---|---|
| *G01R 33/565* | (2006.01) |
| *G01R 33/48* | (2006.01) |
| *A61B 5/055* | (2006.01) |
| *G01R 33/561* | (2006.01) |
| *G06N 3/02* | (2006.01) |
| *G01R 33/58* | (2006.01) |

(52) U.S. Cl.
CPC ........ *G01R 33/56554* (2013.01); *A61B 5/055* (2013.01); *G01R 33/4818* (2013.01); *G01R 33/5617* (2013.01); *G01R 33/58* (2013.01); *G06N 3/02* (2013.01)

(58) Field of Classification Search
CPC .......... G01R 33/56554; G01R 33/4818; G01R 33/5617; G01R 33/58; A61B 5/055; G06N 3/02
See application file for complete search history.

(56) References Cited

U.S. PATENT DOCUMENTS

| | | |
|---|---|---|
| 5,378,985 A | 1/1995 | Hinks |
| 5,652,514 A | 7/1997 | Zhang |
| (Continued) | | |

OTHER PUBLICATIONS

Chen et al.,Data-driven self-calibration and reconstruction for non-cartesian wave-encoded single-shot fast spin echo using deep learning., J Magn Reson Imaging. Mar. 2020;51(3):841-853.

*Primary Examiner* — Dixomara Vargas
(74) *Attorney, Agent, or Firm* — Lumen Patent Firm

(57) ABSTRACT

A method for magnetic resonance imaging (MRI) includes steps of acquiring by an MRI scanner undersampled magnetic-field-gradient-encoded k-space data; performing a self-calibration of a magnetic-field-gradient-encoding point-spread function using a first neural network to estimate systematic waveform errors from the k-space data, and computing the magnetic-field-gradient-encoding point-spread function from the systematic waveform errors; reconstructing an image using a second neural network from the magnetic-field-gradient-encoding point-spread function and the k-space data.

8 Claims, 12 Drawing Sheets

(56) References Cited

U.S. PATENT DOCUMENTS

| | | | | |
|---|---|---|---|---|
| 6,239,598 B1* | 5/2001 | Zhang | ................... | G01R 33/58 |
| | | | | 324/307 |
| 6,369,568 B1 | 4/2002 | Ma | | |
| 6,957,097 B2* | 10/2005 | Park | ................... | A61B 5/0263 |
| | | | | 600/410 |
| 7,408,345 B2 | 8/2008 | Bammer | | |
| 7,888,935 B1 | 2/2011 | Tan | | |
| 8,248,069 B2* | 8/2012 | Buracas | ............. | A61B 5/0263 |
| | | | | 324/307 |
| 8,934,694 B2* | 1/2015 | Chen | ................... | G06T 11/008 |
| | | | | 382/131 |
| 10,520,573 B2 | 12/2019 | Chen | | |
| 2003/0199750 A1* | 10/2003 | Park | ................... | A61B 5/0263 |
| | | | | 600/410 |
| 2009/0322331 A1* | 12/2009 | Buracas | ............ | G01R 33/4806 |
| | | | | 324/309 |
| 2013/0182932 A1* | 7/2013 | Chen | .............. | G01R 33/56509 |
| | | | | 382/131 |
| 2019/0133542 A1* | 5/2019 | Li | ....................... | A61B 6/5264 |

* cited by examiner

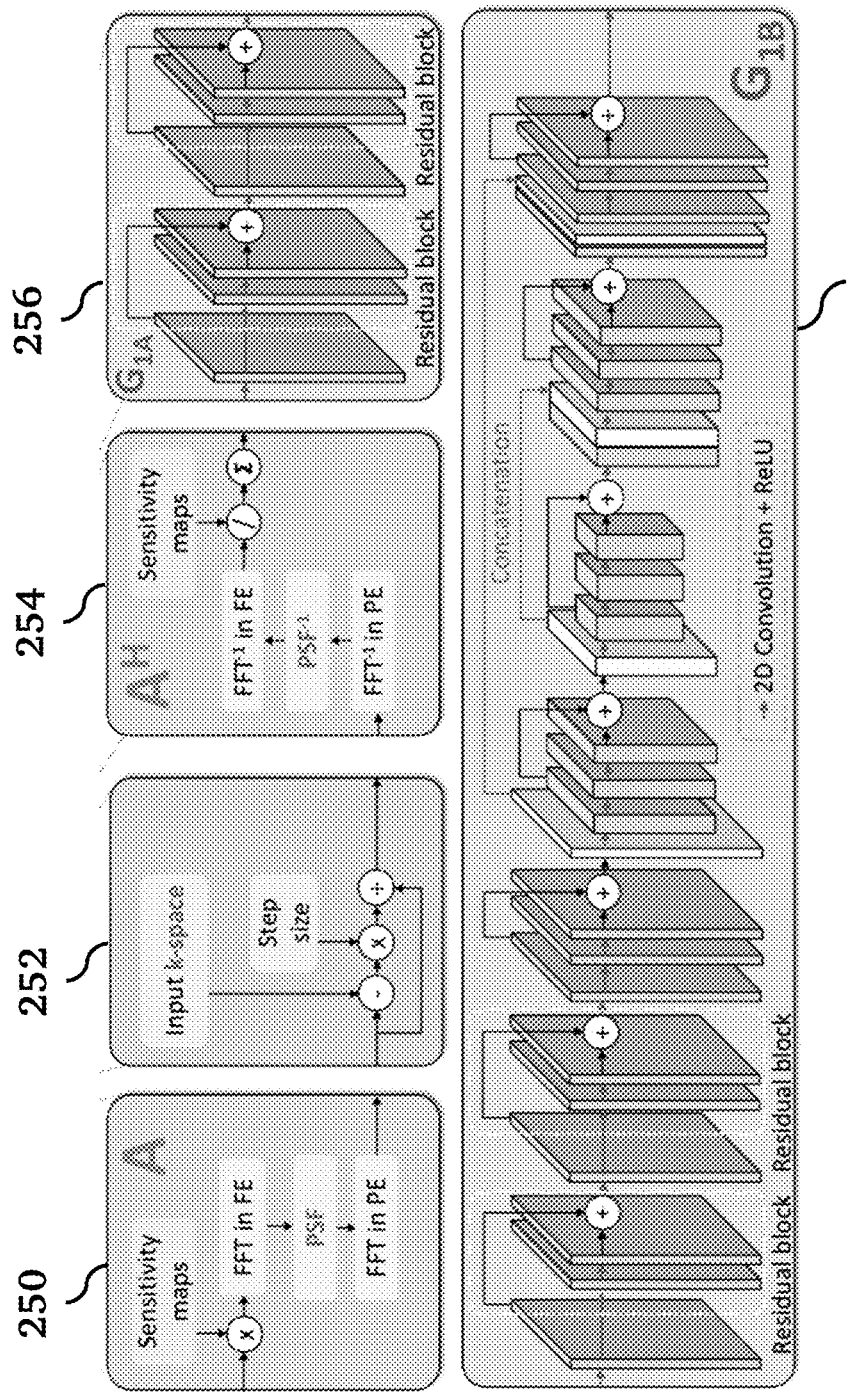

METHOD FOR ESTIMATING SYSTEMATIC IMPERFECTIONS IN MEDICAL IMAGING SYSTEMS WITH DEEP LEARNING

CROSS-REFERENCE TO RELATED APPLICATIONS

This application claims priority from U.S. Provisional Patent Application 62/820,941 filed Mar. 20, 2019, which is incorporated herein by reference.

STATEMENT REGARDING FEDERALLY SPONSORED RESEARCH OR DEVELOPMENT

This invention was made with Government support under contracts HL136965, EB019241, and EB009690 awarded by the National Institutes of Health. The Government has certain rights in the invention.

FIELD OF THE INVENTION

The present invention relates generally to magnetic resonance imaging (MRI). More specifically, it relates to methods for MRI reconstruction using self-calibration of the magnetic-field-gradient-encoding point-spread function.

BACKGROUND OF THE INVENTION

Spin echo (SE) MR sequences provide T2-weighted images are often used clinically. While conventional SE sequences provide high image quality, they are usually slow in acquisition. To accelerate the acquisition of T2-weighted images, single-shot (SS) and multi-shot fast spin echo (FSE) sequences have been developed[1-3]. In these sequences, multiple phase-encoding (PE) signals are acquired after each radio-frequency (RF) pulse. This approach reduces the scan time of T2-weighted imaging to less than a second per slice. However, in abdominal applications, conventional SSFSE (or HASTE) still requires more than 30 seconds to achieve full-abdomen coverage[4-6]. This duration is usually too long for single breath-holds, and may result in degraded image quality due to respiratory and cardiac motion or inconsistency between two separated breath-holds.

Various efforts have been made to accelerate SSFSE imaging. On the hardware side, multi-channel coils with increased number of channels up to 128 have been developed to improve parallel imaging performance and enable higher acceleration factors of up to 8-fold[7]. On the sequence development side, variable refocusing flip angles[8], variable-density sampling[6], and wave encoding[9,10] have been developed to enable compressed sensing reconstruction and improve image sharpness. Among these techniques, wave-encoded SSFSE has been previously demonstrated to achieve improved sharpness and reduced scan time in comparison with standard SSFSE[6].

Despite the improvement of image quality with wave-encoded SSFSE imaging, this imaging technique usually requires extra computation resources and leads to increased reconstruction time[6]. First, wave encoding uses sinusoidal waveforms during the readout. The actual waveform may differ from theoretical waveforms due to systematic imperfections such as gradient delays and eddy currents. Therefore, calibrating the waveform is usually required by either using a calibration scan or performing self-calibration of the point-spread function (PSF). Self-calibration techniques may require additional computation due to iterative optimizations[11,13], which are both computationally expensive and time-consuming. Second, a parallel imaging and compressed sensing (PICS) reconstruction[14-16] is used to reconstruct images from under-sampled wave-encoded k-spaces. This process may require up to 1000 iterations, leading to even longer computation time.

This long total computation time of self-calibration and reconstruction amounts to several minutes per series. This resulting delay to see images may impair clinical workflows, including prescription of subsequent images and detection and correction of issues, such as motion artifacts, incorrect scan prescription, or fat suppression failures. Therefore, acceleration of both self-calibration and reconstruction of wave-encoded SSFSE might lead to greater efficiencies.

Current self-calibration and reconstruction methods for wave-encoded single-shot fast spin echo imaging (SSFSE) requires long computational time, especially when high accuracy is needed.

BRIEF SUMMARY OF THE INVENTION

Recently, data-driven deep-learning-based reconstruction has been developed and applied to various MRI applications to accelerate the speed of image reconstruction and improve image quality[17-20]. Specifically, for SSFSE, variational networks have been used to improve the signal-to-noise ratio and overall image quality of abdominal SSFSE imaging[21-23].

The purpose of this work was to develop and investigate the clinical feasibility of using deep neural networks for data-driven self-calibration and reconstruction of wave-encoded SSFSE to improve the calibration and reconstruction speed and the image quality of abdominal wave-encoded SSFSE imaging.

In one aspect, the invention provides a method for magnetic resonance imaging (MRI) comprising: acquiring by an MRI scanner undersampled magnetic-field-gradient-encoded k-space data; performing a self-calibration of a magnetic-field-gradient-encoding point-spread function using a first neural network to estimate systematic waveform errors from the k-space data, and computing the magnetic-field-gradient-encoding point-spread function from the systematic waveform errors; reconstructing an image using a second neural network from the magnetic-field-gradient-encoding point-spread function and the k-space data.

In some embodiments, the magnetic-field-gradient-encoded k-space data is wave-encoded k-space data, and the magnetic-field-gradient-encoding point-spread function is a wave-encoding point-spread function.

In some embodiments, acquiring the undersampled magnetic-field-gradient-encoded k-space data comprises using a magnetic-field-gradient-encoded single shot fast spin echo sequence with variable density sampling.

In some embodiments, the systematic waveform errors comprise calibrated gradient time delay and isocenter location shift of magnetic-field-gradient-encoding gradients.

In some embodiments, the systematic waveform errors further comprise a scaling factor defining a ratio of actual and theoretical magnetic-field-gradient-encoding gradient amplitudes.

In some embodiments, performing a self-calibration of the magnetic-field-gradient-encoding point-spread function comprises using the first neural network to estimate systematic waveform errors from the k-space data, a theoretical maximum magnetic-field-gradient-encoding gradient amplitude, and a theoretical isocenter location.

In some embodiments, the second neural network used for reconstructing the image comprises multiple steps, wherein each step comprises a gradient update and a proximal step with a learned regularization network operator with trained parameters.

BRIEF DESCRIPTION OF THE SEVERAL VIEWS OF THE DRAWINGS

FIG. 2C is a processing pipeline and network architecture showing details about A, $A^H$, gradient updates, and neural network architecture $G_{1a}$ used in the first three steps of FIG. 2B.

FIG. 2D shows the neural network architecture $G_{1b}$ used in the last step of FIG. 2B.

DETAILED DESCRIPTION OF THE INVENTION

Embodiments of the present invention apply to various types of magnetic field gradient encoding. For the purposes of definiteness, the following description will focus primarily on embodiments using wave encoding.

Data Acquisition with a Wave-Encoded SSFSE Sequence

Figure 1A:
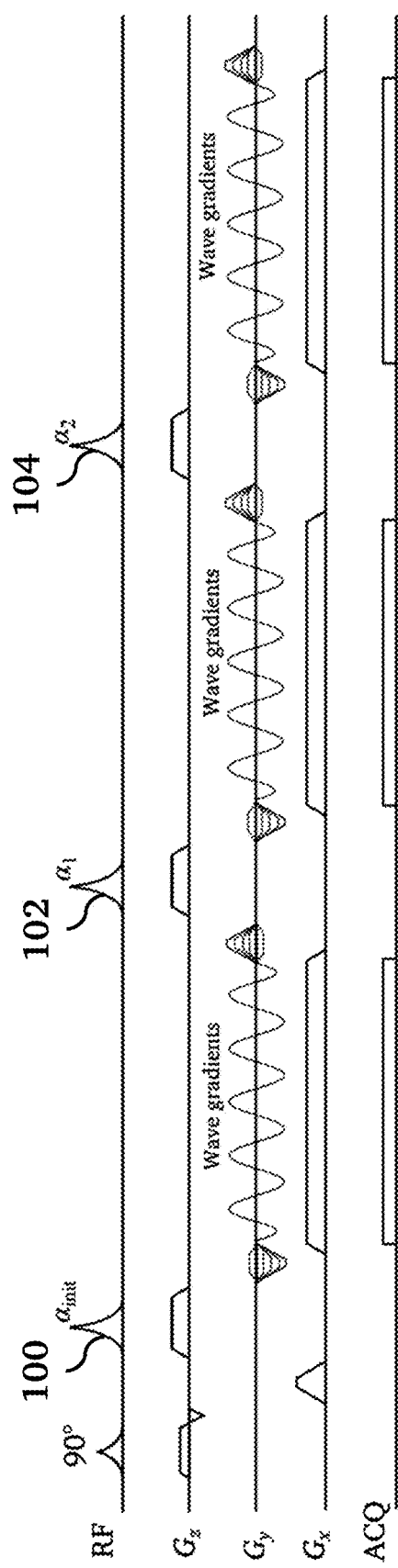
FIG. 1A is an illustration of wave-encoded SSFSE imaging showing a pulse sequence diagram of wave-encoded SSFSE with the first three echoes shown. Wave-encoding gradients were played during the readouts in the phase-encoding gradient axis.

According to one embodiment of the invention, a wave-encoded single-shot fast spin echo (SSFSE) sequence with variable refocusing flip angles and variable-density sampling is used to acquire under-sampled wave-encoded k-space data. To achieve wave encoding, a sinusoidal wave-encoding gradient pulse sequence was played out on the phase encoding (PE) gradient axis during the readout of each frequency-encoding (FE, $k_x$) line. FIG. 1A is a pulse sequence diagram of the wave-encoded SSFSE with the first three echoes 100, 102, 104 shown. Detailed design of the sinusoidal waveform followed the reference[6], with the area of the first and last sinusoidal lobes reduced by 50% and a maximum amplitude between 8.5 mT/m and 12.5 mT/m. This maximum amplitude was inversely proportional to the readout field-of-view to account for object signal spreading induced by wave encoding[9]. At the same time, a readout oversampling factor of 1.6 was used in all scans to capture all spreading signal.

Figure 1B:
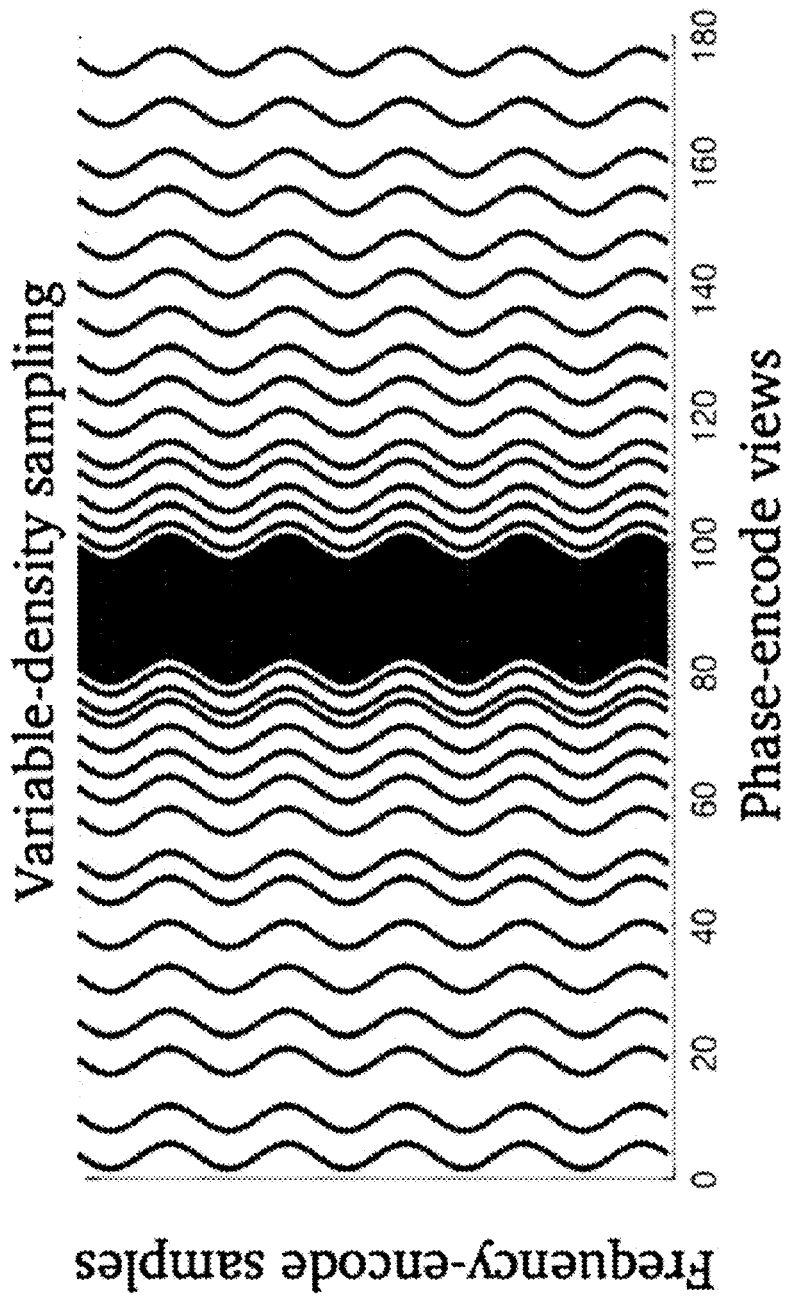
FIG. 1B is an illustration of a variable-density sampling pattern for self-calibrated wave encoding. Due to the modulation of wave-encoding gradients, wave-encoded trajectories are curved.
Figure 1C:
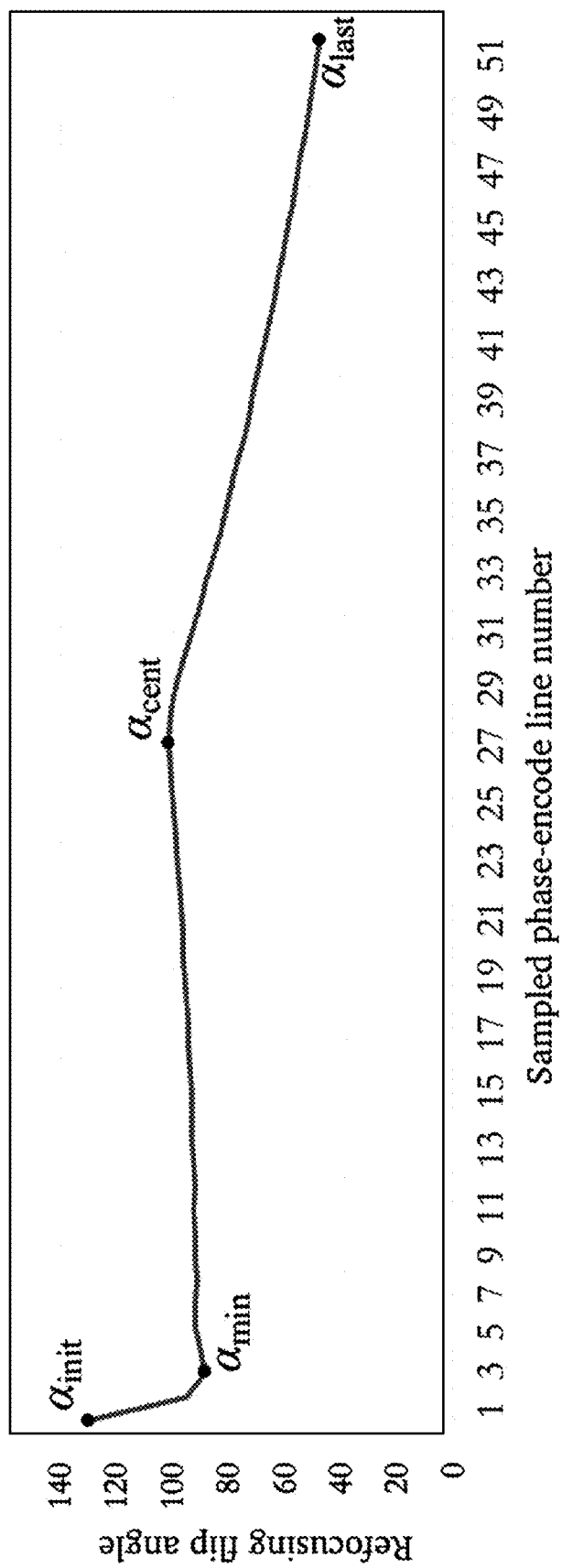
FIG. 1C is a graph of variable refocusing flip angles for wave-encoded SSFSE. The refocusing flip angles are controlled by four parameters: initial, minimum, center, and last flip angles.

Variable-density sampling and variable refocusing flip angle were used in the sequence to enable full-Fourier acquisitions[6]. The sampling pattern contains pseudo-random sampling PE locations and a central coil calibration region of around 20 PE views. FIG. 1B is an illustration of the variable-density sampling pattern for self-calibrated wave encoding. Due to the modulation of wave-encoding gradients, wave-encoded trajectories are curved. Variable refocusing flip angle was also used in the sequence[8] to minimize blurring from T2 delay. The variable refocusing flip angle echo train was mainly controlled by four determining flip angles: the initial flip angle $a_{init}$, the minimum flip angle $a_{min}$, the center flip angle $a_{cent}$, and the last flip angle $a_{last}$. FIG. 1C illustrates these variable refocusing flip angles for wave-encoded SSFSE. The refocusing flip angles are controlled by four parameters: initial, minimum, center, and last flip angles. According to a previous study[5], optimal refocusing flip angles for abdominal scans started with $a_{init}$ of 130°, decreased to $a_{min}$ of 90°, increased to $a_{cent}$ of 100°, and then decreased to $a_{last}$ of 45°. As the spin-echo signal did not reach a stabilized state in the beginning of the echo train, the first four echoes were discarded.

PSF Calibration Using Data-Driven Estimation of Systematic Imperfections

Wave encoding usually requires waveform and PSF calibration due to systematic imperfections, such as gradient delays, eddy currents, and inaccurate isocenter locations. In practice, to correct this effect to the first order, a scaling factor η defining the ratio between the actual and theoretical wave-encoding gradient amplitudes, a gradient delay time Δt, and an isocenter location shift Δy are introduced into the ideal waveform $g_{y0}(t)$. This modified waveform is then used to correct the wave-encoding PSF[6]. With these parameters in consideration, the actual gradient is $\eta \cdot g_{y0}(t-\Delta t)$, and the actual wave-encoding PSF can be expressed as $$PSF[n,k]=\exp(i\gamma \cdot \int_0^{\tau[n]} \eta \cdot g_{y0}(t-\Delta t) dt \cdot (y[k]-\Delta y)), \quad [1]$$

where $\gamma$ is the gyromagnetic ratio, sampling time $\tau[n]$ (from the beginning of the readout) and spatial location $y[k]$ define the two dimensions of the PSF with n defined as the index along the frequency encoding direction and k defined for phase encoding, and $\eta$, $\Delta t$, and $\Delta y$ are three parameters for correcting PSF errors due to systematic imperfections. Previously, systematic-imperfection-related parameters were determined by maximizing the normalized gradient of reconstructed zero-padding images with an iterative Nelder-Mead simplex method[23].

According to embodiments of the invention, we replaced this iterative optimization process with a deep neural network. In our imaging systems, we observed a constant scaling factor $\eta$ of 0.995. Therefore, the scaling factor was kept constant in this study. In this case, the entire problem of determining systematic imperfection parameters can be described as $$\Delta \hat{t}, \Delta \hat{y} = G_0(s, g_{max}, y_{iso} | \theta_0), \quad [2]$$

where $G_0$ is a trained neural network with three inputs: (1) the raw under-sampled, coil-combined, and wave-encoded k-space s, (2) the theoretical maximum wave-encoding gradient amplitude $g_{max}$, and (3) the theoretical isocenter location $y_{iso}$. Coil combination was performed by averaging the signal from all coil channels for fast computation. Both values of $g_{max}$ and $y_{iso}$ are determined based on the scan prescription. $\Delta \hat{t}$ and $\Delta \hat{y}$ represent the calibrated time delay and the isocenter shift of the wave-encoding gradients. Trained network parameters are denoted as $\theta_0$. There are 42,635,810 trainable parameters in $\theta_0$ in total.

Figure 2A:
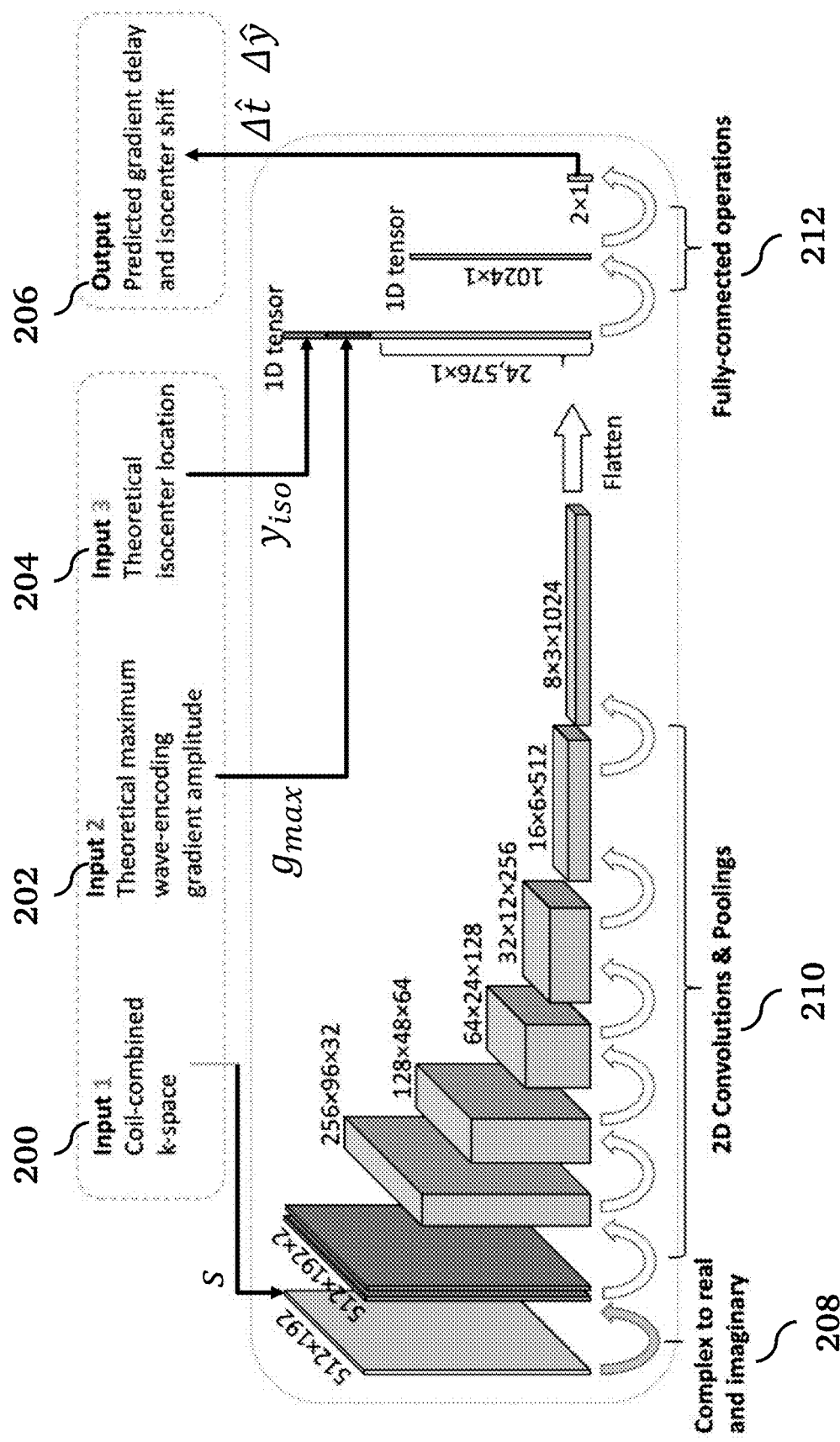
FIG. 2A shows a processing pipeline and network architecture of data-driven calibration of wave-encoded SSFSE according to an embodiment of the invention. The input of this network includes the coil-combined k-space, the theoretical maximum wave-encoding gradient amplitude, and the theoretical isocenter location of the acquisition. This network architecture contains a complex to real and imaginary operation, six convolutional and pooling layers with ReLU activations, and two fully-connected layers. The final output includes the predicted gradient delay and the predicted shift between the actual and theoretical isocenters.

The network architecture of $G_0$ is illustrated in FIG. 2A. The input of this network includes the coil-combined k-space 200, the theoretical maximum wave-encoding gradient amplitude 202, and the theoretical isocenter location of the acquisition 204. The final output 206 includes the predicted gradient delay and the predicted shift between the actual and theoretical isocenters. This network architecture contains a complex to real and imaginary operation 208, six convolutional and pooling layers with ReLU activations 210, and two fully-connected layers 212.

The first step 208 converts complex numbers into real numbers by stacking the real and imaginary components together in the feature dimension. The second step 210 contains 2D operations. This step uses 2D convolutional operations and 2D pooling operations to extract k-space-domain features of the input under-sampled wave-encoded k-space. The third step 212 contains 2D to 1D operations that flatten the output of the second step 210 into a one-dimensional vector and concatenate this vector with the input maximum wave-encoding gradient amplitude $g_{max}$ 202 and the input theoretical isocenter location $y_{iso}$ 204. After two fully-connected operations 212, the network outputs $\Delta \hat{t}$ and $\Delta \hat{y}$ 206, and these two parameters are used to generate the actual wave-encoding PSF according to Eq. 1.

Image Reconstruction Using Deep Neural Networks and Gradient Updates

With the calibrated wave-encoding PSF determined as described above, a data-driven reconstruction using unrolled networks is used to recover the image. Each step of the data-driven reconstruction can be formulated as a gradient update $m^{(k)} - 2tA^H(Am^{(k)}-s)$ and a proximal step with a learned regularization network operator $G_1^{(k)}$ with trained parameters $\theta_1^{(k)}$. The entire step can be expressed as $$m^{(k+1)} = G_1^{(k)}(m^{(k)} - 2tA^H(Am^{(k)}-s)|\theta_1^{(k)}), \quad [3]$$

where $m^{(k+1)}$ and $m^{(k)}$ refer to the output and input images of the $k^{th}$ step. $m^{(k+1)}$ is also the input of the $(k+1)^{th}$ step. 2t refers to the step size of the gradient update[17]. In this embodiment, four steps of iterations in Eq. 3 were used. The entire network is denoted as $G_1$, with 1,247,044 trainable parameters. s is the partially acquired (i.e., undersampled) wave-encoded k-space data, and A describes the wave-encoding model. As described previously, the wave-encoding model can be expressed as $A = D \cdot \mathcal{F}_y \cdot PSF \cdot \mathcal{F}_x \cdot E$. In this model, D is the k-space sampling operator, E is the coil sensitivity operator, PSF is the calibrated wave-encoding PSF, and $\mathcal{F}_y$ and $\mathcal{F}_x$ are the Fourier transform operators in PE and FE directions. In this embodiment, PSF was computed using the data-driven approach described above.

Figure 2B:
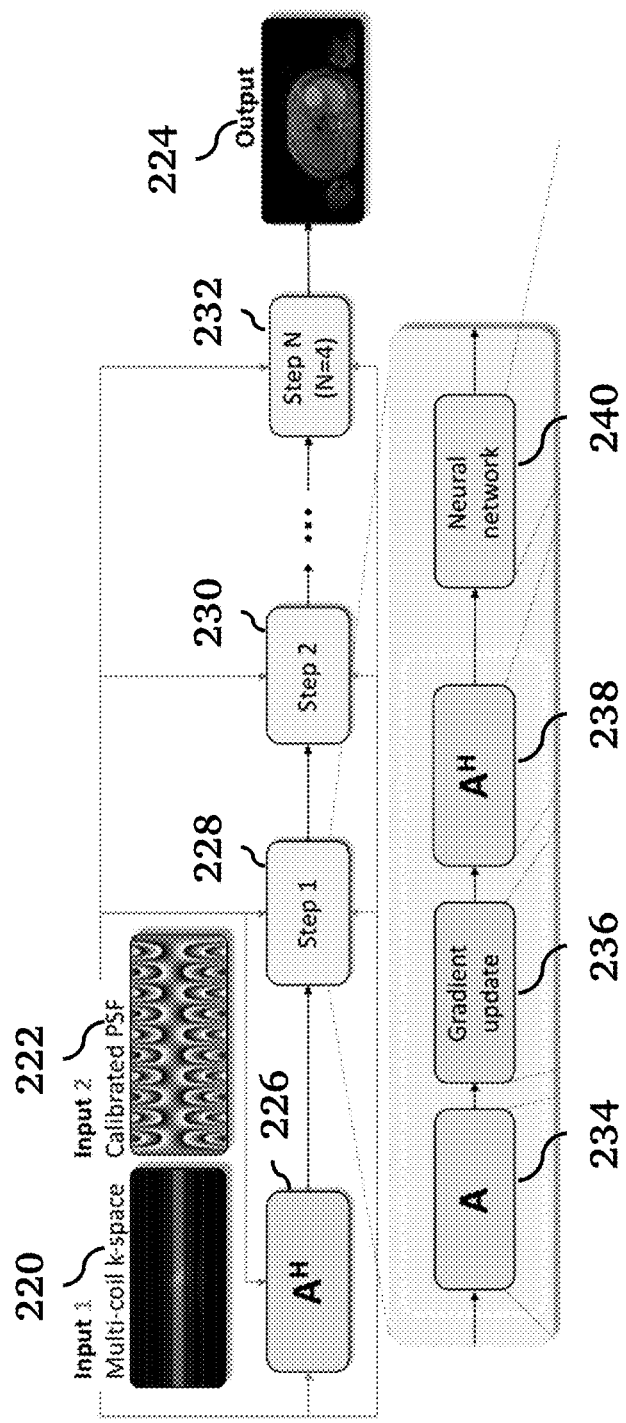
FIG. 2B is a processing pipeline for data-driven reconstruction of wave-encoded SSFSE. k-Spaces from multiple coil channels and the calibrated PSF generated with the data-driven self-calibration method were used as the input. After generating an initial image with $A^H$, where A represents a chain of operations to generate images from multi-coil k-space, four steps of data-driven reconstruction blocks were used to perform gradient updates and neural network computations.

The implementation of the sequence of $G_1^{(k)}$ operators is shown in FIG. 2B. The k-space data 220 from multiple coil channels and the calibrated PSF 222 generated with the data-driven self-calibration method were used as the input. The output of the sequence of steps is image 224. First, an initial image is generated with $A^H$ 226, where A represents a chain of operations to generate images from multi-coil k-space. The result is then processed by a sequence of steps 228, 230, 232 of data-driven reconstruction blocks which perform gradient updates and neural network computations. The output of the last step 232, is image 224. In this implementation, there are four steps, each containing the application of operator A 234 followed by a gradient update 236, the operator $A^H$ 238, and a neural network 240, which are shown in more detail in FIG. 2C as blocks 250, 252, 254, 256. The network 256 is a relatively small five-layer network that contains a 2D convolutional layer and two residual blocks. Residual blocks were chosen because it has been shown to have stable training for deep networks. Each residual block contains two 2D convolutional layers. Rectified linear unit (ReLU) activations and a kernel size of 3 by 3 were used after each convolutional layer. This network architecture $G_{1A}$ 256 is used for all the steps except the last one (232, FIG. 2B) where the network architecture $G_{1B}$ 258 is used instead, as shown in FIG. 2D. The network architecture $G_{1B}$ 258 begins with the same five-layer network $G_{1A}$ (256, FIG. 2C) followed by a three-stage u-net[25] because u-net has been shown to yield state-of-the-art performance for image-to-image translation tasks. The u-net contains bypass concatenations between layers with same sizes as those network $G_{1A}$ (256, FIG. 2C). This u-net also uses a kernel size of 3×3. Circular padding was used in all convolutional operations[17].

Network Training and Model Deployment

To train the PSF-calibration network $G_0$, conventional optimization-based self-calibration approach[6] are used to generate ground truth labels of the gradient delay $\Delta t$ and the isocenter shift $\Delta y$. Network parameters $\theta_0$ in $G_0$ are minimized through $3 \times 10^6$ steps of stochastic gradient descent with an Adam optimizer[26], a learning rate of 0.005, a batch size of 20, and $l_1$ loss.

To train the reconstruction networks in $G_1$, conventional PICS reconstruction[6] in the BART toolbox[27] is used to generate ground truth labels of the image. Network parameters $\theta_1$ in $G_1$ are minimized through $2.5 \times 10^6$ steps of stochastic gradient descent with an Adam optimizer, a learning rate of 0.005, a batch size of 4, and $l_1$ loss. Coil sensitivity maps are estimated directly using zero-padding reconstructions and SENSE[14] models based on calibrated wave-encoding PSFs.

The networks $G_0$ and $G_1$ are trained separately on 15,783 2D wave-encoded SSFSE abdominal images on GE MR750 3T scanners collected with Institutional Review Board approval. After training of the networks is done, this data-driven pipeline can be clinically deployed and used to perform image reconstruction of wave-encoded SSFSE with constant and low computational cost.

Figure 3:
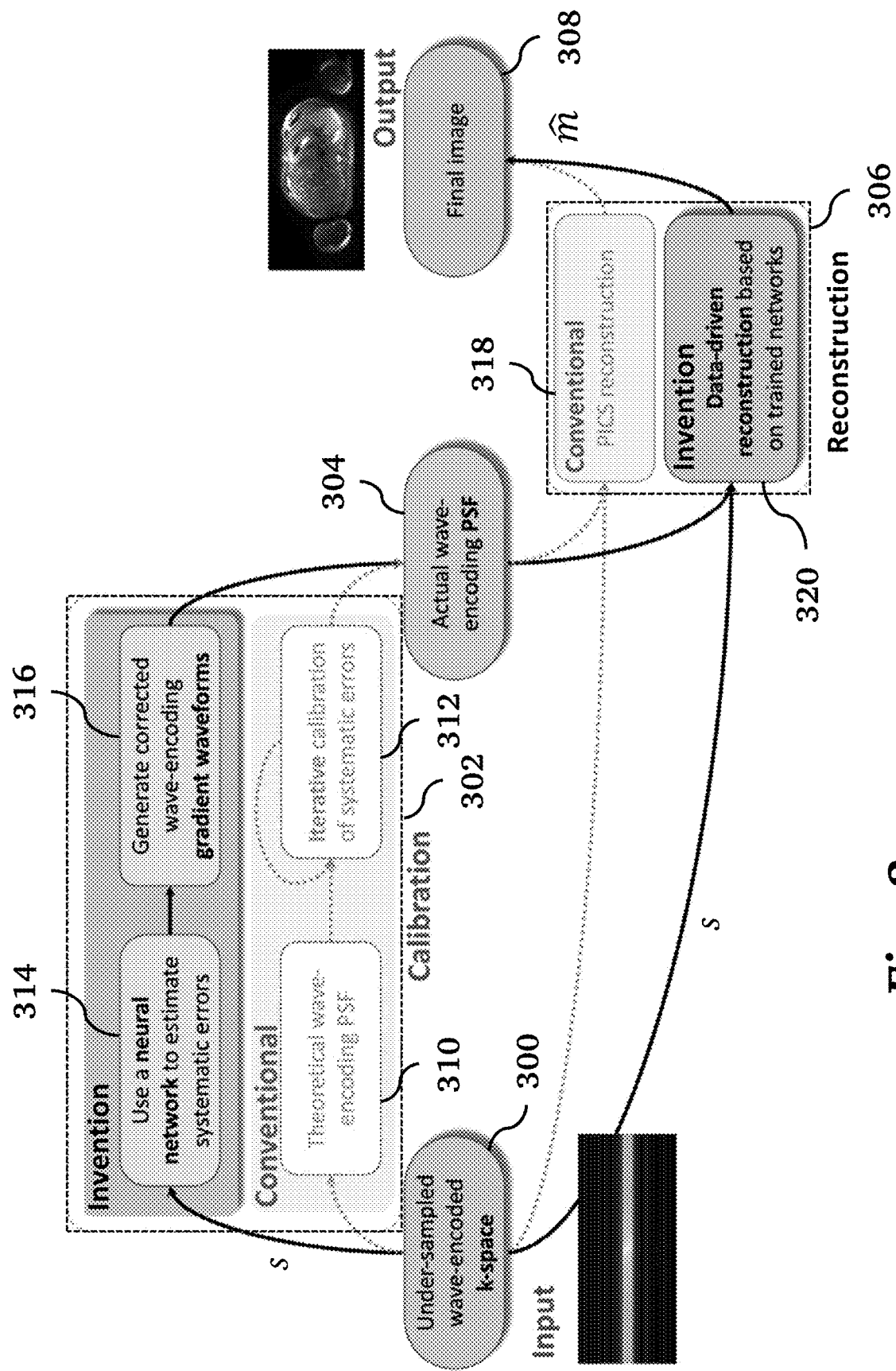
FIG. 3 is a processing pipeline of a data-driven self-calibration and reconstruction of the invention, in comparison with conventional self-calibration and PICS reconstruction (in light gray). In the first stage, under-sampled wave-encoded k-space is used to generate the actual wave-encoding PSF with a trained neural network. In the second stage, the under-sampled wave-encoded k-space and the calibrated wave-encoding PSF are used to generate the final images with the data-driven reconstruction of the invention using gradient updates and trained neural networks.

The complete pipeline of the self-calibration and reconstruction method is illustrated in FIG. 3 in comparison with the conventional PSF self-calibration and reconstruction workflow (in light gray). The entire calibration and reconstruction problem can be formulated as:

$$\hat{m} = G_1(s, f_{PSF}(G_0(s, g_{max}, y_{iso}|\theta_0))|\theta_1), \quad [4]$$

where $\hat{m}$ is the reconstructed image, $f_{PSF}$ is a function that generates the calibrated wave-PSF based on Eq. 1, and s is the partially acquired (i.e., undersampled) wave-encoded k-space data. As shown in the FIG. 3, the under-sampled wave-encoded k-space data 300 is input to the calibration stage 302 which produces the actual wave-encoding PSF 304. The under-sampled wave-encoded k-space data 300 and the calibrated wave-encoding PSF 304 are then input to the reconstruction stage 306 to produce the reconstructed image 308.

In the PSF calibration stage 302, the conventional technique includes a theoretical wave-encoding PSF 310 and iterative self-calibration 312. According to the present invention, these are replaced with a trained neural network $G_0$ 314 to output wave-encoding gradient delays and isocenter shifts, $\hat{\Delta t}$ and $\hat{\Delta y}$, as described above in relation to FIG. 2A. The wave-encoding gradient delays and isocenter shifts are then used in step 316 to generate the PSF 304.

In the reconstruction stage 306, the conventional iterative PICS reconstruction 318 is replaced with data-driven reconstruction 320, as described above in relation to FIGS. 2B, 2C, 2D.

Clinical Scanning

To test the method, clinical abdominal scanning was performed on 29 consecutive adult patients (18 males, 11 females, ranging from 24 to 77 years) on a 3T MRI scanner using a 32-channel torso coil and a 2D multi-slice wave-encoded SSFSE imaging sequence. The acquisition plane was axial and PE direction was anterior/posterior. Each subject was asked to breath hold during each acquisition period. Fat-suppression was incorporated with a spectral-spatial-selective pulse. Field of view was optimized to each patient's anatomy (30-42 cm). Additional parameters are shown in Table 1. All images were reconstructed using (1) conventional PSF self-calibration and PICS reconstruction using a combination of C/C++(the BART software package[27]) and Python with 50 iterations and an $l_1$-wavelet regularization coefficient of 0.002, and (2) an embodiment of the data-driven self-calibration and reconstruction method of an embodiment the invention, implemented in TensorFlow.

Figure 4:
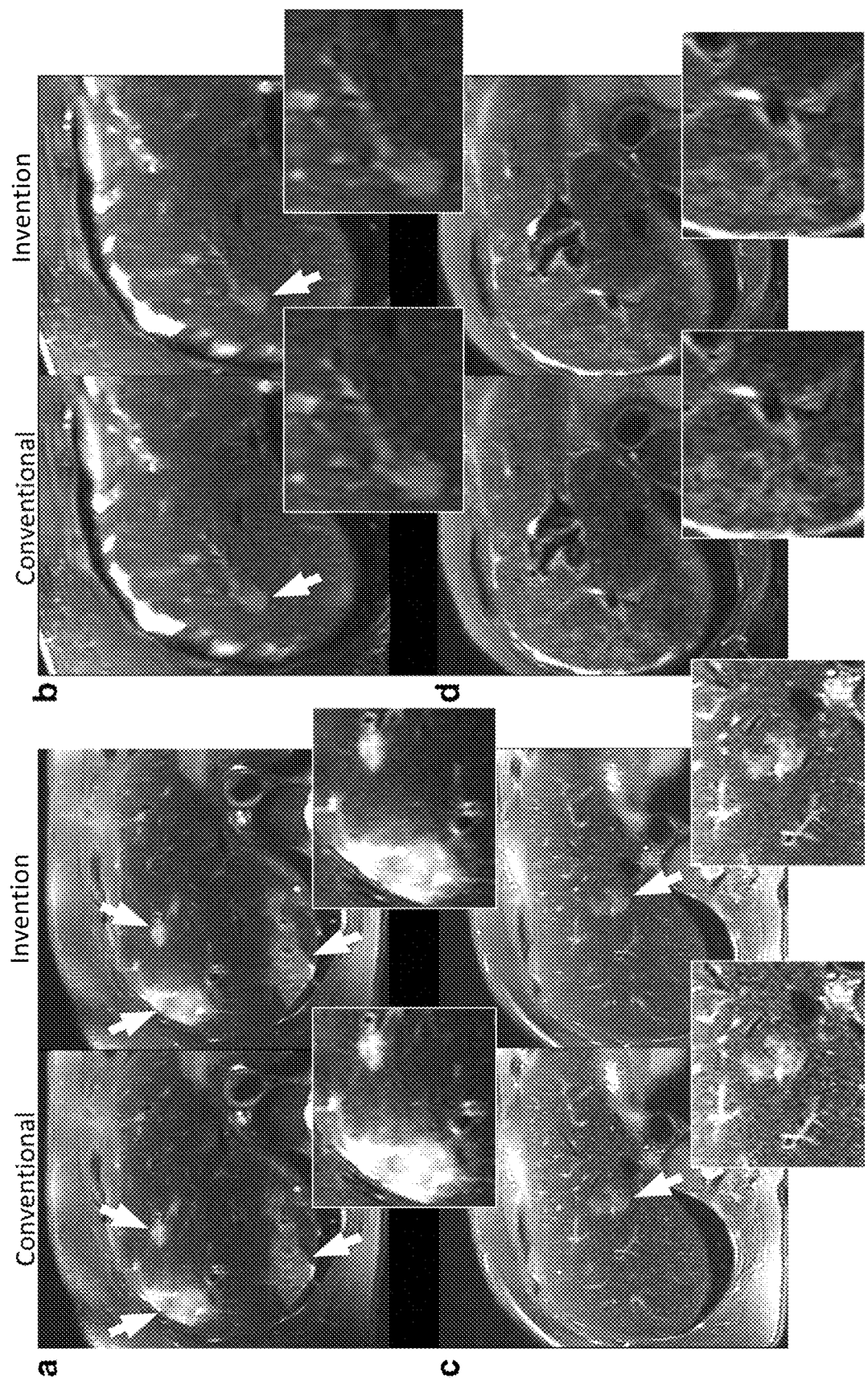
FIG. 4 shows example images of the liver using conventional reconstruction and the data-driven reconstruction of the invention.

Representative images containing the liver are shown in FIG. 4. The data-driven calibration and reconstruction approach of the present invention (columns 2 and 4) achieved comparable structural delineation of the liver and the lesions (indicated by white arrows in FIG. 4) compared to the conventional approach using iterative calibration and PICS reconstruction (columns 1 and 3). Improvements in perceived signal-to-noise ratio were observed in the reconstruction of the invention, with reduced level of graininess. The method of the invention and the conventional approach yielded similar image contrast. Significant artifacts were observed in neither approach.

Figure 5:
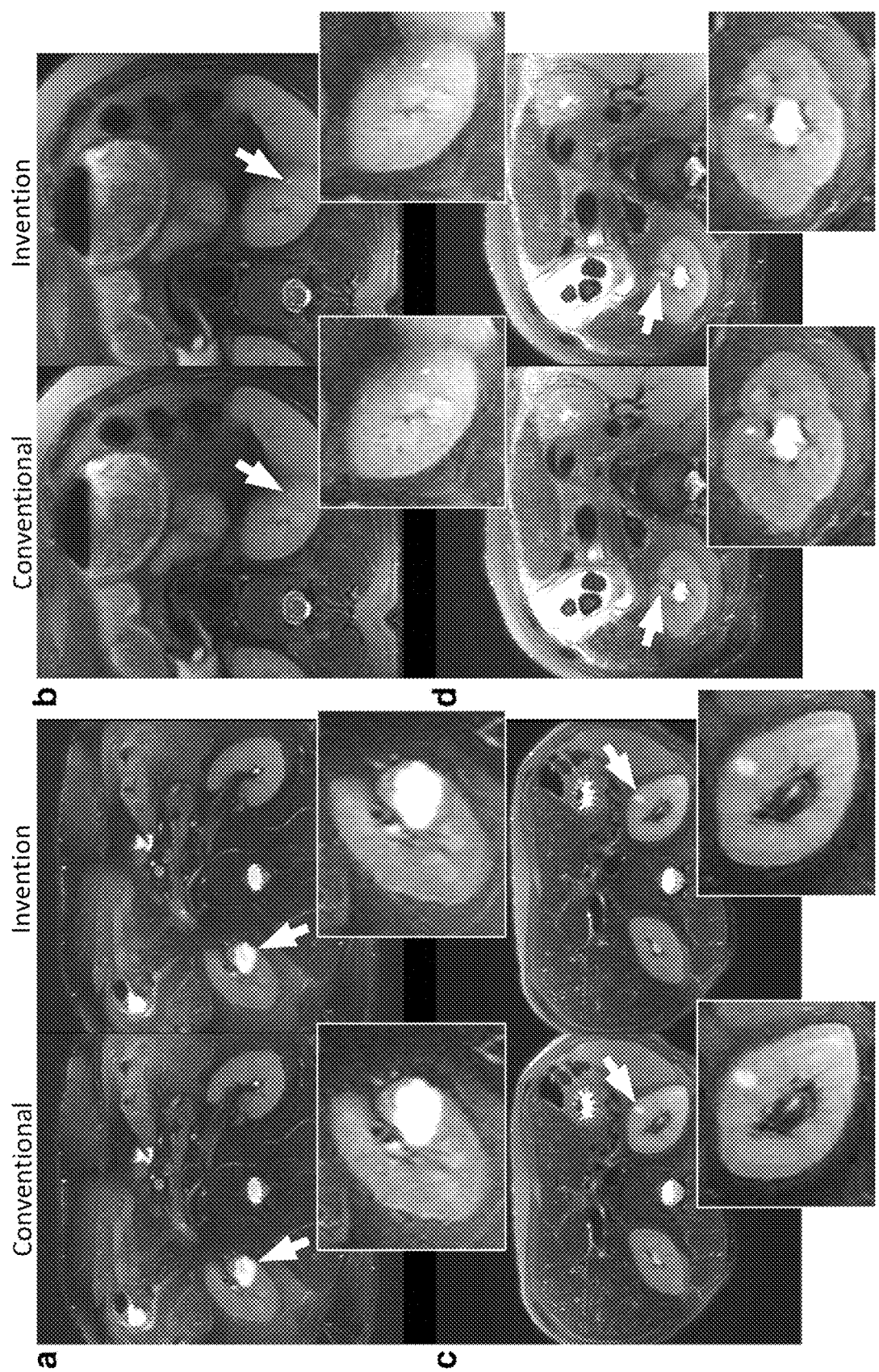
FIG. 5 shows example images of the kidneys using conventional reconstruction and the data-driven reconstruction of the invention.

Representative images containing the kidneys are shown in FIG. 5. Comparable structural delineation and sharpness of the kidney were observed in all examples using both the reconstruction method of the invention (columns 2 and 4) and the conventional method (columns 1 and 3). The data-driven reconstruction of the invention was able to reconstruct very small lesions, as indicated by white arrows in FIG. 5. Similar contrast between these two methods was achieved. No significant artifacts were observed in both methods.

Figure 6:
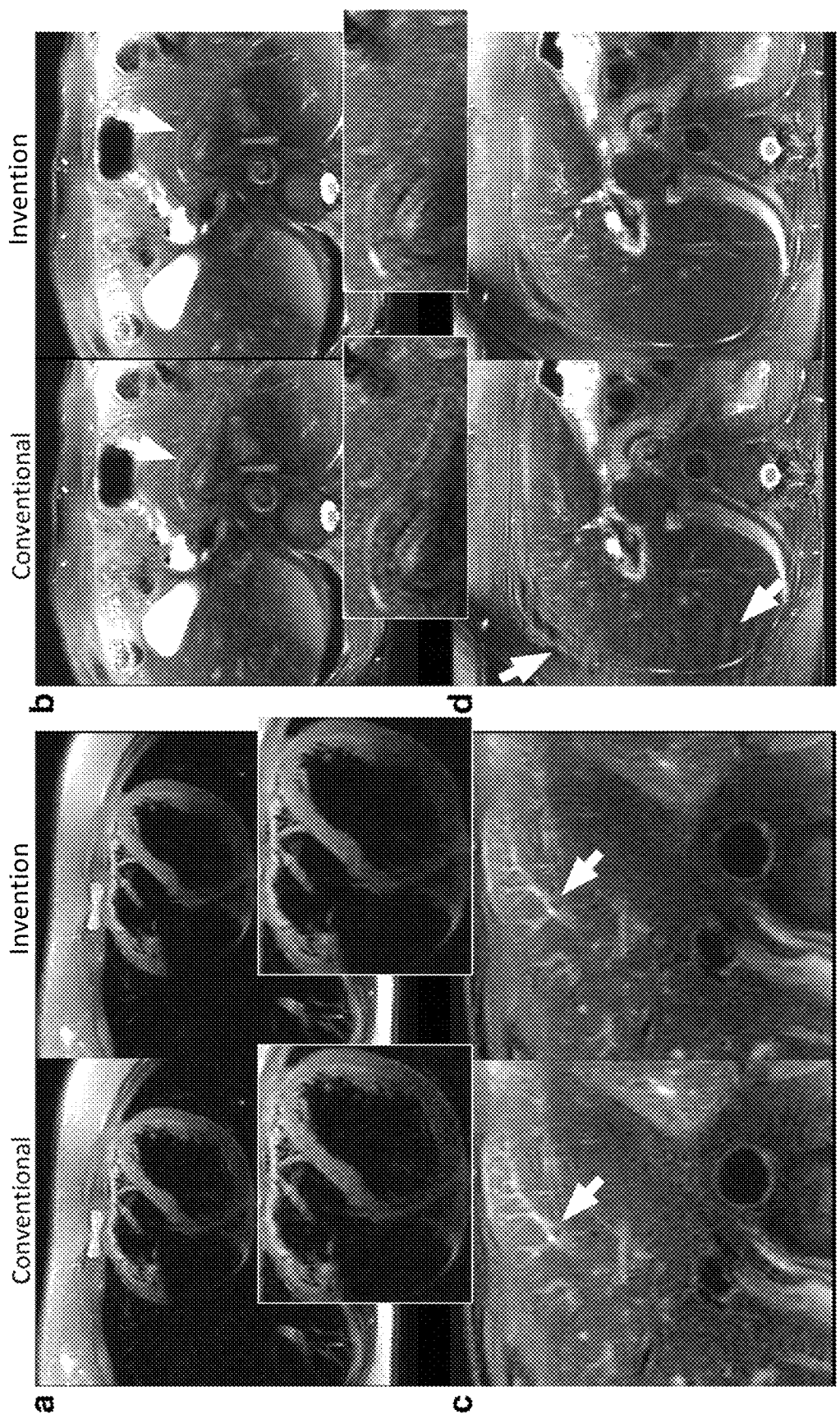
FIG. 6 shows example images containing other regions of interest or artifacts using the conventional reconstruction and the data-driven reconstruction of the invention.

Representative images of other regions of interest are shown in FIG. 6. The approach of the present invention yielded comparable structural delineation of these regions and was able to reconstruct the detailed structures. Similar contrast was achieved in these regions. Reduced perceived noise can be observed and the data-driven approach reduces the phase-wrapping artifacts occurred in the conventional reconstruction.

Mean difference of the gradient delays between the data-driven approach and the conventional approach was 0.0497 msec. Mean difference of the isocenter shifts between the data-driven approach and the conventional approach was 0.1006 pixel.

Individual Assessments of Image Quality

Reconstructed clinical images were independently evaluated using a semi-quantitative grading system that rated noise, contrast, sharpness, general artifacts other than motion-related artifacts, and confidence of detecting liver lesions. The scores were predetermined on a scale from −2 to 2 (Table 2). Positive values favor the data-driven method of the present invention, and negative values favor the conventional self-calibration and PICS reconstruction. Three readers independently scored each pair of the reconstructed images in a blinded, randomized order.

Wilcoxon signed-rank tests were used to test the null hypothesis that there was no significant difference between the conventional self-calibration and reconstruction approach and the data-driven approach of the invention for each reader and their average scores. Inter-observer variability was assessed utilizing a Fleiss' kappa statistic. The kappa coefficients were interpreted as almost perfect (0.8-1), substantial (0.6-0.8), moderate (0.4-0.6), fair (0.2-0.4), slight (0-0.2), and poor (<0). A two-tailed P value of under 0.05 was considered as statistical significance. The Fleiss' kappa statistic for the data-driven reconstruction of the invention vs. the conventional comparison indicated fair agreement among the readers in image sharpness (0.21) and confidence of detecting liver lesions (0.24), and slight agreement among the readers in perceived noise (0.13), general artifacts (0.09), and image contrast (0.04).

Figure 7A:
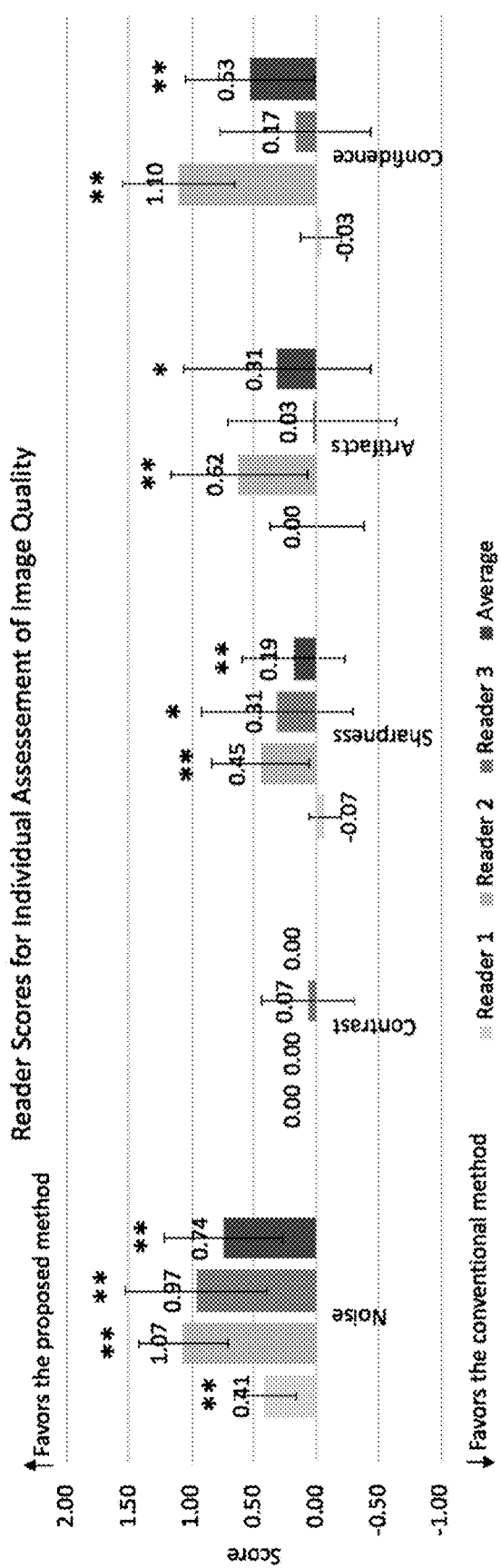
FIG. 7A is a chart of overall image quality assessments for the conventional reconstruction and the data-driven reconstruction of the invention from different readers, and their average scores.

Results of individual assessments of image quality are shown in FIG. 7A. The data-driven self-calibration and reconstruction approach of the invention showed significantly reduced perceived noise and no difference in image contrast. Statistically different results with P<0.05 were marked with (*). Statistically different results with P<0.005 were marked with (**). Error bars are standard error of the mean.

Non-inferior image sharpness, artifacts, and diagnosis confidence for the data-driven approach of the invention were observed by all three readers. Non-inferior image quality means the approach of the invention has significantly improved image quality with P<0.05 or non-significant difference in image quality (with P values no less than 0.05) when compared to the conventional approach. Pairwise comparison of the average scores from the readers demonstrated significance in improved image sharpness, reduced artifacts, and confidence of detecting liver lesions, with mean scores of 0.23, 0.22, and 0.41, and P values of 0.001, 0.04, and 0.0003.

Evaluation of Online Computation Time

Online computation time was recorded for each patient scan using both conventional iterative self-calibration and PICS reconstruction method and the data-driven calibration and reconstruction method of an embodiment of the invention under identical hardware settings with GPU-optimized computations (two Intel Xeon CPU E5-2670 v3 @ 2.30 GHz CPUs with 24 cores each, 256 Gb RAM, and two NVIDIA TITAN X GPUs). The ratio of the average computation time between these two approaches was calculated. A t-test was performed to test the null hypothesis that there is no significant difference between the computation time of the conventional approach and the approach of the invention. A two-tailed P value of under 0.05 was considered as statistical significance.

Figure 7B:
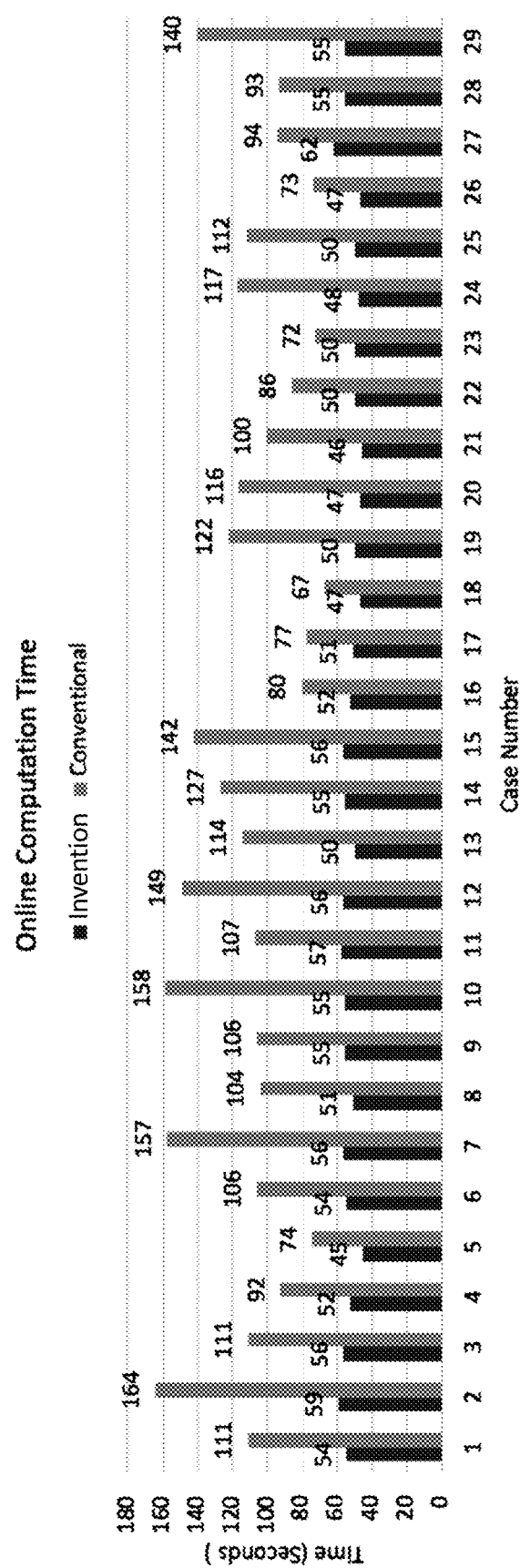
FIG. 7B is a chart of an image reconstruction time decrease.

An image reconstruction time decrease was consistently achieved in all 29 cases as shown in FIG. 7B. The average online computation time of the data-driven calibration and reconstruction of the invention to reconstruct the entire volume was 52.4±4.2 seconds, while conventional calibration and reconstruction took 108.3±27.2 seconds. Statistical analysis shows significant difference between the computation time of the approach of the invention and the conventional approach ($P<0.0001$). This comparison indicated an average reduction factor of 2.1 using the data-driven reconstruction approach of the invention, corresponding to a 51.6% decrease in computation time.

Embodiments of the invention provide a data-driven calibration and reconstruction method for reconstructing clinically-relevant images of wave-encoded SSFSE imaging. By replacing iterative wave-encoding PSF calibration and PICS reconstruction with trained neural network models, the approach of the invention brought the reconstruction time closer to the acquisition duration, reducing the lags and queues in the clinical workflow. At the same time, the approach of the invention achieved reduction in perceived noise while preserving the contrast and sharpness of the current iterative approach. This approach also demonstrated a potential in reducing ghosting artifacts caused by limited field-of-views.

The invention may be implemented with different network architectures. In the self-calibration stage, the goal was to output two systematic imperfection parameters, i.e., the gradient delay and the isocenter shift between theoretical locations and actual locations. This type of output requires the neural network to reduce layer size as the layer goes deeper to extract features in the k-space domain. In the reconstruction stage, a five-layer neural network was used as a regularization function along with gradient updates. This relatively shallow design may also reduce the chance of overfitting and generating hallucinations in the early stage of the data-driven reconstruction. In the last step, a u-net was designed to improve the capacity of the network in reducing general artifacts and improving the signal-to-noise ratio. There are in total four iterations of gradient update blocks and neural network blocks. The number of iterations was empirically chosen according to a previous study[28] to achieve a tradeoff between computational speed and reconstruction performance. Other embodiments may use other architectures to achieve other balances in tradeoffs.

The calibration stage and the reconstruction stage can be trained together or separately. In tests of the embodiments presented above, training of the calibration network took 148.8 hours and training of the reconstruction network took 2331.3 hours on a single NVIDIA GTX 1080Ti GPU. Training these two stages separately improves the flexibility of model deployment, as these two stages can be upgraded independently in clinical systems. Separate training may also benefit the training speed, as there are fewer unknown weights to learn in each training step, compared with joint training of all networks. At the same time, it is more convenient to check the correctness of the imperfection outputs and terminate the training of either the calibration network or the reconstruction networks when these networks are trained separately. Inaccurate PSF mainly results in ghosting artifacts near the edges of the imaging target. Therefore, improvements of PSF accuracy will reduce the level of ghosting artifacts. In these tests, ghosting artifacts due to PSF inaccuracy were hardly visible. Accuracy of the data-driven reconstruction model will affect most aspects of the final image, including sharpness, noise level, and ghosting artifacts. Therefore, the reconstruction model usually plays a more important role in the final image quality than the calibration model.

The data-driven approach of the invention reduces the total online reconstruction time by performing straightforward computations using the trained networks. In conventional calibration of the wave-encoding PSF, we notice an instability in the number of required optimization steps before convergence. In our tests, the conventional approach was been optimized for parallel computation among multiple slices. There are 48 CPU cores on our computation hardware; therefore, when the number of slices is greater than 48, the total computation time nearly doubles because a second round of computation is required for slices other than the first 48 slices. When the number of acquired slices is no larger than 48, we saw computation times of around 80 sec. When there were more than 48 slices, the computation time was around 150 sec using the conventional approach. This factor increases the instability of reconstruction time for the conventional approach. For the data-driven calibration approach, the number of computations is fixed after the models are trained, thus this approach has a relatively stable computation time. Similar behaviors can be observed in the reconstruction stage. For different number of slices (smaller or greater than 48), the computation time is relatively stable, as the reconstruction of multiple slices can be parallelized on the GPU. This time increases at a scale of 1-10 sec with increasing number of slices. The computation time of the approach of the invention in different reduction factors is also stable, as this time is only related to the number of operations in the model.

The data-driven approach of the invention reduced the perceived noise in reconstructed images by learning an optimal regularization among a large number of existing datasets. This observation is consistent with a previous study[23]. The improvement in perceived signal-to-noise ratio may be attributed to the diversity of the training dataset. Since our training dataset contains scans with different parameters, conditions, and thus different noise level, the trained model learns an average reconstruction of this large amount of reconstructions. Therefore, compared with conventional PICS reconstruction with a fixed regularization parameter, the resultant data-driven reconstruction achieves a more uniform perceived signal-to-noise ratio. Image-domain convolutions may also contribute to the reduction in noise level, as these operations tend to average the noise over image patches defined by the receptive field of neural networks.

The approach of the invention is able to capture small structures and maintain comparable image sharpness and contrast with respect to the conventional iterative reconstruction. This capability can be attributed to the unrolled pipeline used in the data-driven reconstruction of the invention. This pipeline contains four steps of gradient updates, which promote the data consistency between the reconstructed images and the acquired raw signal. Accurate calibration of the gradient delays and the isocenter shifts also enables good image sharpness and structural delineation comparable to the conventional reconstruction. The approach of the invention reduced phase-wrapping artifacts, as most images in the training dataset contain no phase-wrapping artifact. Pre-selection of images for training may help improve the reconstruction performance. The removal of phase wrapping artifacts using deep neural networks also means potential loss of small lesions. In this case, gradient update blocks in the reconstruction model can help ensure good data-consistency with the partially acquired k-space. The diagnostic information provided by removing phase-wrapping artifacts needs to be further evaluated.

Gradient amplitude changes and gradient delays are typically caused by eddy currents in the gradient system of the scanner. Isocenter shifts are usually caused by gradient field inhomogeneity. Therefore, for difference scanners, these imperfections may be different, and the performance of the method of the invention with extreme imperfections still needs to be evaluated. The scaling factor of maximum wave-encoding gradient was fixed in the calibration stage based on our observations that the scaling factor was stable among the scanners we have access to within a period of approximately a month. For a different constant gradient scaling factor, it is necessary to retrain the calibration network. When unstable or different scaling factors are observed on different scanners, it is also possible to include the scaling factor as an extra output parameter in the training and prediction stage while keeping the same architecture for other parts of the network. In this case, the output size of the calibration network contains three variables. The number of iterations and the regularization coefficient were also fixed in our study. This is based on previous studies on variable-density SSFSE imagine[4-6]. However, for applications in other regions of interest, these parameters may be different and need to be chosen empirically.

Because the approach of the invention is data-driven, a sufficient amount of data should be used. For certain applications where it may be difficult or time-consuming to acquire these datasets[29-31] training data may be simulated.

In the embodiments described above, the acquisition matrix size is fixed for the data-driven approach. There are potential solutions for reconstructing scans with varying matrix sizes[17], which may be used if needed. For example, the input may be cropped, padded, and/or resized to the ensure uniform matrix size. Although the tests described above were focused on wave-encoded SSFSE applications in clinical abdominal scans with fat suppression and a reduction factor of 3.5, the method of the invention may be used for other reduction factors and in other applications. For example, other applications include Cartesian encoding, Spiral encoding, Cones encoding, Propeller encoding, Radial encoding, and other non-Cartesian encoding approachs.

In conclusion, the data-driven self-calibration and reconstruction of the invention achieves an average 2.1-fold acceleration of the online computation and reduced perceived noise while maintaining non-inferior image contrast, image sharpness, artifacts, and confidence of detecting liver lesions of standard reconstruction. Together with wave-encoded SSFSE acquisition, this imaging approach provides fast and robust T2-weighted imaging as well as a fast and efficient clinical workflow.

It should be emphasized that, although the description above has focused on wave encoding as an example of a hybrid non-Cartesian sampling technique, the methods are generally applicable for reconstructing images from general non-Cartesian k-space data using data-driven deep-learning techniques according to the same techniques. The pipeline for various types of non-Cartesian sampling techniques is generally the same as that described above for wave-encoding. The estimated parameters may be adapted for different encoding methods, and the reconstruction algorithm may be adapted for different encodings. The input for other encodings may be in other domains, e.g. the k-space (spatial-frequency domain) instead of the image domain, and the network architecture can be adapted (with different operations/layers, etc.).

REFERENCES

1. Semelka R C, Kelekis N L, Thomasson D, Brown M A, Laub G A. HASTE M R imaging: description of technique and preliminary results in the abdomen. J Magn Reson Imaging 1996; 6:698-699.
2. Feinberg D A, Hale J D, Watts J C, Kaufman L, Mark A. Halving MR imaging time by conjugation: demonstration at 3.5 kG. Radiology 1986; 161:527-531.
3. Mugler J P. Optimized three-dimensional fast-spin-echo MRI. J Magn Reson Imaging 2014; 39:745-767.
4. Loening A M, Litwiller D V, Saranathan M, Vasanawala S S. Increased Speed and Image Quality for Pelvic Single-Shot Fast Spin-Echo Imaging with Variable Refocusing Flip Angles and Full-Fourier Acquisition. Radiology 2017; 282:561-568.
5. Loening A M, Saranathan M, Ruangwattanapaisarn N, Litwiller D V, Shimakawa A, Vasanawala S S. Increased speed and image quality in single-shot fast spin echo imaging via variable refocusing flip angles. J Magn Reson Imaging 2015; 42:1747-1758.
6. Chen F, Taviani V, Tamir J I, Cheng J Y, Zhang T, Song Q, Hargreaves B A, Pauly J M, Vasanawala S S. Self-Calibrating Wave-Encoded Variable-Density Single-Shot Fast Spin Echo Imaging. J Magn Reson Imaging 2018; 47(4):954-966.
7. Hardy C J, Giaquinto R O, Piel J E, Rohling AAS K W, Marinelli L, Blezek D J, Fiveland E W, Darrow R D, Foo T K. 128-channel body MRI with a flexible high-density receiver-coil array. J Magn Reson Imaging 2008; 28(5): 1219-1225.
8. Busse R F, Brau A C, Vu A, Michelich C R, Bayram E, Kijowski R, Reeder S B, Rowley H A. Effects of refocusing flip angle modulation and view ordering in 3D fast spin echo. Magn Reson Med 2008; 60:640-649.
9. Bilgic B, Gagoski B A, Cauley S F, Fan A P, Polimeni J R, Grant P E, Wald L L, Setsompop K. Wave-CAIPI for highly accelerated 3d imaging. Magn Reson Med 2015; 73:2152-2162.
10. Gagoski B A, Bilgic B, Eichner C, Bhat H, Grant P E, Wald L L, Setsompop K.RARE/turbo spin echo imaging with Simultaneous Multislice Wave-CAIPI. Magn Reson Med 2015; 73:929-938.
11. Chen F, Zhang T, Cheng J Y, Shi X, Pauly J M, Vasanawala S S. Auto-calibrating motion-corrected wave-encoding for highly accelerated free-breathing abdominal MRI. Magn Reson Med 2017; 78(5):1757-1766.
12. Chen F, Zhang T, Cheng J Y, Taviani V, Hargreaves B, Pauly J, Vasanawala S, inventors; General Electric Co, Leland Stanford Junior University, assignee. System and method for performing wave-encoded magnetic resonance imaging of an object. U.S. patent application Ser. No. 15/481,893. 2018 May 24.
13. Cauley S F, Setsompop K, Bilgic B, Bhat H, Gagoski B, Wald L L. Autocalibrated wave-CAIPI reconstruction; Joint optimization of k-space trajectory and parallel imaging reconstruction. Magn Reson Med 2017; 78(3):1093-1099.
14. Uecker M, Lai P, Murphy M J, Virtue P, Elad M, Pauly J M, Vasanawala S S, Lustig M. ESPIRiT: an eigenvalue approach to autocalibrating parallel MRI: where SENSE meets GRAPPA. Magn Reson Med 2014; 71:990-1001.
15. Lustig M, Donoho D, Pauly J M. Sparse MRI: The application of compressed sensing for rapid MR imaging. Magn Reson Med 2007; 58:1182-1195.
16. Shi X, Ma X, Wu W, Huang F, Yuan C, Guo H. Parallel imaging and compressed sensing combined framework for accelerating high-resolution diffusion tensor imaging using inter-image correlation. Magn Reson Med 2015; 73(5):1775-1785.
17. Cheng J Y, Chen F, Sandino C, Mardani M, Pauly J M, Vasanawala S S. Compressed Sensing: From Research to Clinical Practice with Data-Driven Learning. arXiv preprint arXiv:1903.07824.
18. Cheng J Y, Chen F, Alley M T, Pauly J M, and Vasanawala S S. Highly Scalable Image Reconstruction using Deep Neural Networks with Bandpass Filtering. arXiv preprint arXiv:1805.03300.
19. Yang Y, Sun J, Li H, and Xu Z. ADMM-Net: A Deep Learning Approach for Compressive Sensing MRI. NIPS 2017; 10-18.
20. Adler J, Öktem O. Learned primal-dual reconstruction. IEEE transactions on medical imaging. 2018; 37(6):1322-32.
21. Hammernik K, Klatzer T, Kobler E, Recht M P, Sodickson D K, Pock T, Knoll F. Learning a variational network for reconstruction of accelerated MRI data. Magn Reson Med 2018; 79(6):3055-3071.
22. Chen F, Taviani V, Malkiel I, Cheng J Y, Tamir J I, Shaikh J, Chang S T, Hardy C J, Pauly J M, Vasanawala S S. Variable-density single-shot fast spin-echo MRI with deep learning reconstruction by using variational networks. Radiology. 2018; 289(2):366-373.
23. Olsson D M, Nelson L S. The nelder-mead simplex procedure for function minimization. Technometrics 1975; 17:45-51.
24. Krizhevsky A, Sutskever I, Hinton G E. Imagenet classification with deep convolutional neural networks. Advances in neural information processing systems 2012; 1097-1105.
25. Ronneberger O, Fischer P, Brox T. U-net: Convolutional networks for biomedical image segmentation. In International Conference on Medical image computing and computer-assisted intervention 2015; 234-241.
26. Kingma D P, Ba J. Adam: A method for stochastic optimization. arXiv preprint arXiv:1412.6980.
27. Uecker M, Ong F, Tamir J I, Bahri D, Virtue P, Cheng J Y, Zhang T, Lustig M. Berkeley advanced reconstruction toolbox. Proc. Intl. Soc. Mag. Reson. Med 2015; 23:2486.
28. Mardani M, Sun Q, Donoho D, Papyan V, Monajemi H, Vasanawala S, Pauly J. Neural proximal gradient descent for compressive imaging. In Advances in Neural Information Processing Systems 2018; 9573-9583.
29. Chen F, Cheng J Y, Pauly J M, Vasanawala S S. Semi-Supervised Learning for Reconstructing Under-Sampled MR Scans. Proc. Intl Soc Mag Reson Med 2019; 27:4649.
30. Chen F, Shi X, Chen S, Johnson E M, Chen B, Ren G, Wei X, Wang S, Ying K. Accelerated model-based proton resonance frequency shift temperature mapping using echo-based GRAPPA reconstruction. Magnetic resonance imaging 2015; 33 (2):240-245.
31. Hu Y, Levine E G, Tian Q, Moran C J, Wang X, Taviani V, Vasanawala S S, McNab J A, Daniel B A, Hargreaves B L. Motion-robust reconstruction of multishot diffusion-weighted images without phase estimation through locally low-rank regularization. Magn Reson Med 2019; 81(2):1181-1190.

TABLE 1

Scan Parameter Summary

| | |
|---|---|
| Refocusing flip angles (initial/minimum/central/last) | 130°/90°/100°/45° |
| Slice thickness | 5 mm |
| Slice gap | 0 |
| Matrix | 320 × 180 |
| FOV | 300-420 mm × 240-336 mm |
| Number of slices | 35-64 |
| Echo time (TE) | 90.9-93.1 msec |
| Repetition time (TR) | 436.5-560.6 msec |
| Total scan time | 16.9-32.8 sec |
| Bandwidth | 488.2 Hz/pixel |
| Acceleration factor for variable density sampling | 3.5 |
| Sampling pattern | Variable-density sampling (51 acquired PE views) with an auto-calibration region (20 PE views) |
| Proportion of k-space coverage | 1 (full) |

TABLE 2

Scoring Criteria for Conventional Self-Calibration and Reconstruction vs. Data-Driven Self-Calibration and Reconstruction of the Invention

| | Favors A | | | Favors B | |
|---|---|---|---|---|---|
| Score | −2 | −1 | 0 | 1 | 2 |
| Noise | A with decreased graininess with improved diagnostic capability | A with decreased graininess without diagnostic impact | Equivalent | B with decreased graininess without diagnostic impact | B with decreased graininess with improved diagnostic capability |
| Contrast | A with good contrast between liver/spleen AND renal cortex/medulla | A with good contrast between liver/spleen OR renal cortex/medulla | Equivalent | B with good contrast between liver/spleen OR renal cortex/medulla | B with good contrast between liver/spleen AND renal cortex/medulla |

TABLE 2-continued

Scoring Criteria for Conventional Self-Calibration and Reconstruction
vs. Data-Driven Self-Calibration and Reconstruction of the Invention

|  | Favors A | | | Favors B | |
| --- | --- | --- | --- | --- | --- |
| Score | −2 | −1 | 0 | 1 | 2 |
| Sharpness | not seen in B A with increased sharpness with improved diagnostic capability | not seen in B A with increased sharpness without diagnostic impact | Equivalent | not seen in A B with increased sharpness without diagnostic impact | not seen in A B with increased sharpness with improved diagnostic capability |
| Artifacts (besides cardiac motion related nonuniformity) | A with decreased artifacts to the point of improved diagnostic capability | A with decreased artifacts without diagnostic impact | Equivalent | B with decreased artifacts without diagnostic impact | B with decreased artifacts to the point of improved diagnostic capability |
| Confidence of detecting liver lesions | A with improved confidence of detecting liver lesions in more than half of the images | A with improved confidence of detecting liver lesions in fewer than half of the images | Equivalent | B with improved confidence of detecting liver lesions in fewer than half of the images | B with improved confidence of detecting liver lesions in more than half of the images |

The invention claimed is:

1. A method for magnetic resonance imaging (MRI) comprising:
   acquiring by an MRI scanner undersampled magnetic-field-gradient-encoded k-space data;
   performing a self-calibration of a magnetic-field-gradient-encoding point-spread function using a first neural network to estimate systematic waveform errors from the k-space data, and computing the magnetic-field-gradient-encoding point-spread function from the systematic waveform errors;
   reconstructing an image using a second neural network from the magnetic-field-gradient-encoding point-spread function and the k-space data.

2. The method of claim 1 wherein the magnetic-field-gradient-encoded k-space data is wave-encoded k-space data.

3. The method of claim 1 wherein the magnetic-field-gradient-encoding point-spread function is a wave-encoding point-spread function.

4. The method of claim 1 wherein acquiring the undersampled magnetic-field-gradient-encoded k-space data comprises using a magnetic-field-gradient-encoded single shot fast spin echo sequence with variable density sampling.

5. The method of claim 1 wherein the systematic waveform errors comprise calibrated gradient time delay and isocenter location shift of magnetic-field-gradient-encoding gradients.

6. The method of claim 5 wherein the systematic waveform errors further comprise a scaling factor defining a ratio of actual and theoretical magnetic-field-gradient-encoding gradient amplitudes.

7. The method of claim 1 wherein performing a self-calibration of the magnetic-field-gradient-encoding point-spread function comprises using the first neural network to estimate systematic waveform errors from the k-space data, a theoretical maximum magnetic-field-gradient-encoding gradient amplitude, and a theoretical isocenter location.

8. The method of claim 1 wherein the second neural network used for reconstructing the image comprises multiple steps, wherein each step comprises a gradient update and a proximal step with a learned regularization network operator with trained parameters.

* * * * *